United States Patent [19]

Smithers

[11] Patent Number: 4,902,712

[45] Date of Patent: * Feb. 20, 1990

[54] FLUOROALKANE DERIVATIVES

[75] Inventor: Michael J. Smithers, Macclesfield, United Kingdom

[73] Assignee: Imperial Chemical Industries plc, London, England

[*] Notice: The portion of the term of this patent subsequent to Feb. 7, 2006 has been disclaimed.

[21] Appl. No.: 861,331

[22] Filed: May 9, 1986

[30] Foreign Application Priority Data

May 10, 1985 [GB] United Kingdom ................ 8511892

[51] Int. Cl.⁴ .................. A61K 31/335; C07D 319/06
[52] U.S. Cl. ..................................... 514/452; 549/375; 548/579; 546/184; 544/358; 544/109
[58] Field of Search ............... 549/375; 514/452, 184, 514/191, 227, 315; 556/170; 544/109, 358; 546/184; 548/579

[56] References Cited

U.S. PATENT DOCUMENTS 4,567,197 1/1986 Brewster et al. .................. 514/452

FOREIGN PATENT DOCUMENTS 94239 11/1983 European Pat. Off. ............ 549/375

*Primary Examiner*—Nicky Chan
*Attorney, Agent, or Firm*—Cushman, Darby & Cushman

[57] ABSTRACT

The invention describes the novel compound 4(Z)-6-([2,4,5-cis]-4-o-hydroxyphenyl-2-trifluoromethyl-1,3-dioxan-5-yl)hexenoic acid of formula I and its pharmaceutically acceptacle salts and pharmaceutical compositions, which are of value in treating certain pulmonary and/or vascular disorders. Also described are various processes for the manufacture of the novel compound and intermediates for use therein.

6 Claims, No Drawings

FLUOROALKANE DERIVATIVES

This invention concerns novel fluoroalkane derivatives and, more particularly, a novel 4(Z)-6-([2,4,5-cis]-2-trifluoromethyl-4-phenyl-1,3-dioxan-5-yl)hexenoic acid which antagonises one or more of the actions of thromboxane $A_2$ (hereafter referred to as "$TXA_2$") and which is of value as a therapeutic agent.

It is known that $TXA_2$ is a potent aggregator of blood platelets and a powerful vasoconstrictor. $TXA_2$ is also a potent constrictor of bronchial and tracheal smooth muscle. $TXA_2$ may therefore be involved in a wide variety of disease conditions, for example ischaemic heart disease such as myocardial infarction, angina, cerebrovascular disease such as transient cerebral ischaemia, migraine and stroke, peripheral vascular disease such as atherosclerosis, microangiopathy, hypertension and blood clotting defects due to lipid imbalance, and pulmonary disease such as pulmonary embolism, bronchial asthma, bronchitis, pneumonia, dyspnoea and emphysema. Accordingly, compounds which antagonise the actions of $TXA_2$ may be expected to have therapeutic value in the prevention or treatment of any one or more or the above mentioned diseases or any other disease conditions in which it is desirable to antagonise the actions of $TXA_2$.

It is also known from our European patent application, publication number 94239, that 4-phenyl-1,3-dioxan-5-ylalkenoic acid derivatives of the formula Z having cis relative stereochemistry at positions 4 and 5 of the doxane ring and wherein Ra and Rb are variously hydrogen, alkyl, halogenoalkyl, alkenyl and optionally substituted aryl or arylalkyl, Rc is hydroxy, alkoxy or alkanesulphonamido, n is 1 or 2, A is ethylene or vinylene, Y is (2–5C)polymethylene optionally substituted by alkyl and benzene ring B bears one or two optional substituents, possess the property of antagonising one or more of the actions of $TXA_2$. We have now discovered and herein lies the basis of our invention that particularly useful $TXA_2$ antagonism is shown by a novel compound of formula Z in which Ra is trifluoromethyl, Rb is hydrogen, benzene ring B is o-hydroxyphenyl, n is 1, A is cis-vinylene, Y is ethylene and Rc is hydroxy.

According to the invention there is provided the novel compound 4(Z)-6-([2,4,5-cis]-4-o-hydroxyphenyl-2-trifluoromethyl-1,3-dioxan-5-yl)hexenoic acid, of formula I set out hereinafter; or a pharmaceutically acceptable salt thereof.

It will be appreciated that the compound of formula I possesses three asymmetric carbon atoms and may exist and be isolated in racemic and optically active forms. The invention includes both the racemic form and that optically active form which is capable of antagonising one or more of the actions of $TXA_2$, it being well known in the art how to prepare individual optical active forms (for example by synthesis from optically active starting materials or by resolution of the racemic form) and how to determine the $TXA_2$ antagonist properties using one or more of the standard tests referred to hereafter.

In the chemical formulae attached hereto, although a particular configuration is shown, this does not necessarily correspond to the absolute configuration.

Particular pharmaceutically acceptable salts of the compound of formula I are, for example, alkali metal and alkaline earth metal salts such as lithium, sodium, potassium, magnesium and calcium salts, aluminium and ammonium salts, and salts with organic amines and quaternary bases forming physiologically acceptable cations such as salts with methylamine, dimethylamine, trimethylamine, ethylenediamine, piperidine, morpholine, pyrrolidine, piperazine, ethanolamine, triethanolamine, N-methylglucamine, tetramethylammonium hydroxide and benzyltrimethylammonium hydroxide.

The compound of formula I may be manufactured by conventional procedures of organic chemistry, well known in the art for the manufacture of structurally analogous compounds, for example those described in our European patent application, publication No. 94239. Such procedures are provided as a further aspect of the invention and are illustrated by the following:

(a) The aldehyde ([2,4,5-cis]-4-o-hydroxyphenyl-2-trifluoromethyl-1,3-dioxan-5-yl)acetaldehyde of the formula II is reacted with a Wittig reagent of the formula $R_3P=CH(CH_2)_2CO_2^-M^+$ wherein R is (1–6C)alkyl or aryl (especially phenyl) and $M^+$ is a cation, for example an alkali metal cation such as the lithium, sodium or potassium cation.

The process is conveniently performed in a suitable solvent or diluent, for example an aromatic solvent such as benzene, toluene or chlorobenzene, an ether such as 1,2-dimethoxyethane, t-butyl methyl ether, dibutyl ether or tetrahydrofuran, in dimethyl sulphoxide or tetramethylene sulphone, or in a mixture of one or more such solvents or diluents. The process is generally performed at a temperature in the range, for example, $-80°$ C. to $40°$ C., but is conveniently performed at or near room temperature, for example in the range $0°$ to $35°$ C.

(b) A phenol derivative of the formula III wherein $R^1$ is a suitable phenol protecting group, for example (1–6C)alkyl (such as methyl or ethyl), allyl, tetrahydropyran-2-yl, acyl (such as acetyl, benzoyl, methanesulphonyl or p-toluenesulphonyl) or trimethylsilyl, is deprotected.

The deprotection conditions used depend on the nature of the protecting group $R^1$. Thus, for example, when it is (1–6C)alkyl (and especially methyl), the deprotection may be carried out by heating with sodium thioethoxide in a suitable solvent (such as N,N-dimethylformamide or N,N-dimethyl-3,4,5,6-tetrahydro-2(1H)-pyrimidinone) at a temperature in the range, for example, $50°$ to $160°$ C. Alternatively, an ethyl or methyl protecting group may be removed by reaction with lithium diphenylphosphide in a suitable solvent (such as tetrahydrofuran or methyl t-butyl ether) at a temperature in the range, for example, $0°$ to $60°$ C. When the protecting group is acyl it may be removed, for example, by hydrolysis in the presence of a base (such as sodium or potassium hydroxide) in a suitable aqueous solvent [such as an aqueous (1–4C)alkanol] at a temperature in the range, for example, $0°$ to $60°$ C. When the protecting group is allyl or tetrahydropyran-2-yl it may be removed for example by treatment with strong acid such as trifluoroacetic acid and when it is trimethylsilyl, it may be removed, for example, by reaction with aqueous tetrabutylammonium fluoride or sodium fluoride using a conventional procedure.

The starting materials for use in the above processes may be made by general procedures of organic chemistry, known for the preparation of structurally related compounds. Thus, the aldehyde of formula II may be obtained, for example, by the methods described in Example 2 hereinafter. The protected phenol derivatives of formula III may be made, for example, by Scheme 1 or by using an analogous procedure to process (a) above using an aldehyde analogous to that of formula II, but wherein the phenol group has been protected with the group $R^1$, such a protected aldehyde being made, for example, by analogy with the formula II aldehyde but omitting a deprotection step.

The necessary Wittig reagents may be obtained by conventional procedures, for example by treating the corresponding phosphonium halides with a strong base such as sodium hydride, lithium diisopropylamide, potassium t-butoxide or butyllithium. They are generally formed in situ just prior to carrying out the condensation process (a) above.

It will be understood that the acid of formula I may also be obtained by other conventional procedures well known in the art, for example by acid or base catalysed hydrolysis of the corresponding esters, amides or nitriles, or by reaction of a p-toluenesulphonyl (tosyl) derivative of formula IV with trifluoro-acetaldehyde (or its hydrate, methyl or ethyl hemiacetal) followed by base catalysed cyclisation of the intermediate hemiacetal of formula V, by analogy with the procedures of Scheme 1.

When a salt of a compound of formula I is required, it may be obtained, for example, by reaction with the appropriate base affording a physiologically acceptable cation, or by any other conventional procedure.

Further, when an optically active form of a the compound of formula I is required, one of the aforesaid processes may be carried out using the appropriate optically active starting material. Alternatively, the racemic form of a compound of formula I may be reacted with an optically active form of a suitable organic base, for example ephedrine, N,N,N-trimethyl(1-phenylethyl)ammonium hydroxide or 1-phenylethylamine, followed by conventional separation of the diastereoisomeric mixture of salts thus obtained, for example by fractional crystallisation from a suitable solvent, for example a (1-4C)alkanol, whereafter the optically active form of said compound of formula I may be liberated by treatment with acid using a conventional procedure for example using an aqueous mineral acid such as dilute hydrochloric acid.

Many of the intermediates defined herein are novel, for example those of formulae III, IV, and V and are provided as further, separate features of the invention. Certain of the intermediates of formula III, for example, the compound 4(Z)-6-([2,4,5-cis]-4-o-methoxyphenyl-2-trifluoromethyl-1,3-dioxan-5-yl)hexenoic acid, also possess $TXA_2$ antagonist properties.

As stated earlier, the compound of formula I is an antagonist of one or more of the actions of $TXA_2$, for example certain of its actions on blood platelets, the vasculature and/or the lung. The antagonism may be demonstrated in one or other of the following standard tests:

(a) The rabbit aortal strip model devised by Piper and Vane (*Nature*, 1969, 223, 29–35) using as agonist a freshly prepared sample of $TXA_2$, generated by addition of arachidonic acid (25 μg) to citrated, platelet rich rabbit plasma (250 μl) and allowing the mixture to aggregate fully over 90 seconds before use; alternatively the $TXA_2$ mimetic agent known as U46619 (described by R. L. Jones et alia in "Chemistry, Biochemistry and Pharmacological Activity of Prostanoids" edited by S. M. Roberts and F. Scheinmann, at page 211; Pergamon Press, 1979) may be used as the agonist;

(b) a blood platelet aggregation test based on that described by Born (Nature, 1962, 194, 927–929) and involving:

(i) aggregating human, citrated, platelet-rich plasma by addition of the $TXA_2$ mimetic agent U46619 so that a dose-response curve is generated;

(ii) generating a dose-response curve for U46619 stimulated platelet aggregation in the presence of increasing amounts of test compound (generally in the range $10^{-5}M$ to $10^{-10}M$); and (iii) calculating a $K_B$ value indicating potency of $TXA_2$ antagonism for the test compound, averaged over several concentrations, from the calculated 50% response value for U46619 aggregation in the presence and absence of test compound; and (c) a bronchoconstriction test involving measuring the inhibition by a test compound of the bronchoconstriction induced in the Konzett-Rossler, anaesthetised guinea-pig model (as modified by Collier and James, *Brit. J. Pharmacol.*, 1967, 30, 283–307) by intravenous administration of the $TXA_2$ mimetic agent, U46619 and involving:

(i) obtaining a cumulative dose-response curve to U46619 induced bronchoconstriction by intravenous administration of constant volumes of increasing concentrations of U46619 (0.2-4 ug/kg) in physiological saline solution and expressing bronchoconstriction as the maximum of that theoretically obtainable with no air flow to the test animal;

(ii) generating a cumulative dose-response curve to U46619 induced bronchoconstriction at 30 minute intervals for 3 hours after oral dosing of test compound; and (iii) calculating a dose-ratio for the test compound (that is the ratio of concentration of U46619 required to cause 50% bronchoconstriction in the presence and absence of test compound) indicating the potency of $TXA_2$ antagonism.

The antagonism of the effects of $TXA_2$ on the vasculature may be demonstrated, for example in rats in the following manner:

(d) Male rats (Alderley Park strain) are anaesthetised with sodium pentobarbital and blood pressure is monitored at the carotid artery. The $TXA_2$ mimetic agent U46619 is administered intravenously at 5 μg/kg via the jugular vein to produce a 20-30 mm Hg (2640-3970 pascal) increase in systolic blood pressure. The procedure is repeated twice to establish reproducibility of the effect. A test compound is then administered either intravenously (via the jugular vein) or orally (via a cannula) directly into the stomach and the animal is challenged with U46619, five minutes after dosing with test compound and then successively every ten minutes until the hypertensive effect of U46619 is no longer blocked.

Further, the antagonism of the effects of $TXA_2$ in vivo may be demonstrated, for example, by assessing the effects of a test compound on the aggregation of blood platelets obtained after administration of test compound to a test animal, such as a rabbit, rat, guinea pig or dog, using standard procedures similar to that described in (a) above. However, when the aggregation of dog platelets is being studied it is necessary to use a predetermined, threshold concentration of the platelet aggregation agent adenosine diphosphate (about $0.4$–$1.2 \times 10^{-6}M$) together with the $TXA_2$ mimetic agent, U46619.

Using the above test procedures (a)-(c), the following representative results have been obtained with the racemic form of the compound of formula I:

Test (a), $pA_2$ 7.58±0.05;

Test (b), $K_B$: $1.32 \times 10^{-8}M$;

Test (c), dose ratio: >40, 2 hours after oral dosing at 0.005 mg/kg.

Similarly, using test procedure (d) referred to above, the racemic form of the compound of formula I produced >60% inhibition of U46619 induced hypertension 1 hour after an oral dose of 0.05 mg/kg.

By way of comparison, the structurally closely related compound 5(Z)-7-([2,4,5-cis]-4-phenyl-2-trifluoromethyl-1,3-dioxan-5-yl)heptenoic acid disclosed, inter alia, in European patent application, publication No. 94239, possesses significantly lower $TXA_2$ antagonist properties. Thus, for example, using test procedures (a) above, it has a $pA_2$ value of 6.52±0.02.

The above results indicate the unexpectedly superior $TXA_2$ antagonist properties possessed by the compound of formula I.

As stated previously, the compound of formula I may be used in the therapy or prevention of diseases or adverse conditions in warm-blooded animals in which it is desirable to antagonise one or more of the actions of $TXA_2$. In general, an acid of formula I will be administered for this purpose by an oral, rectal, intravenous, subcutaneous, intrauscular or inhalation route, so that a dose in the range, for example 0.01–5 mg/kg body weight, will be given up to four times per day, varying with the route of administration, the severity of the condition and the size and age of the patient under treatment.

The compound of formula I will generally be used in the form of a pharmaceutical composition comprising the compound of formula I or, a pharmaceutically acceptable salt thereof, as defined hereinabove, together with a pharmaceutically acceptable diluent or carrier. Such a composition is provided as a further feature of the invention and may be in a variety of dosage forms. For example, it may be in the form of tablets, capsules, solutions or suspensions for oral administration; in the form of a suppository for rectal administration; in the form of a sterile solution or suspension for administration by intravenous or intramuscular injection; in the form of an aerosol or a nebuliser solution or suspension, for administration by inhalation; and in the form of a powder, together with pharmaceutically acceptable inert solid diluents such as lactose, for administration by insufflation.

The pharmaceutical compositions may be obtained by conventional procedures using pharmaceutically acceptable diluents and carriers well known in the art. Tablets and capsules for oral administration may conveniently be formed with an enteric coating, for example comprising cellulose acetate phthalate, to minimise contact of the active ingredient of formula I with stomach acids.

The pharmaceutical compositions of the invention may also contain one or more agents known to be of value in diseases or conditions intended to be treated; for example a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an antihistamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

In addition to its use in therapeutic medicine, the acid of formula I is also useful as a pharmacological tool in the development and standardisation of test systems for the evaluation of the effects of $TXA_2$ in laboratory animals such as cats, dogs, rabbits, monkeys, rats and mice, as part of the search for new therapeutic agents. The acid of formula I may also be used because of their its $TXA_2$ antagonist properties in helping to maintain the viability of blood and blood vessels in warm-blooded animals (or parts thereof) under-going artificial extracorporeal circulation, for example during limb or organ transplants. When used for this purpose the acid of formula I, or a physiologically acceptable salt thereof, will generally be administered so that a steady state concentration in the range, for example, 0.1 to 10 mg. per liter is achieved in the blood.

The invention will now be illustrated in the following non-limiting Examples in which, unless otherwise stated:

(i) evaporations were carried out by rotary evaporation in vacuo;

(ii) operations were carried out at room temperature, that is in the range 18°–26° C. and under an atmosphere of an inert gas such as argon;

(iii) flash column chromatography and medium pressure liquid chromatography (MPLC) were performed on Merck Kieselgel (Art. 9385) obtained from E. Merck, Darmstadt, W. Germany;

(iv) yields are given for illustration only and are not necessarily the maximum attainable;

(v) proton NMR spectra were normally determined at 200 MHz in $CDCl_3$, using tetramethylsilane (TMS) as an internal standard, and are expressed as chemical shifts (delta values) in parts per million relative to TMS using the usual abbreviations for description of major peaks e.g. s, singlet; m, multiplet; t, triplet; br, broad; d, doublet; q, quartet; and (vi) melting points are uncorrected and determined using a Koffler block apparatus.

EXAMPLE 1

A stirred solution of 4(Z)-6-([2,4,5-cis]-4-o-methoxyphenyl-2-trifluoromethyl-1,3-dioxan-5-yl)hexenoic acid (A) (6.47 g) in dry tetrahydrofuran (THF) (15 ml) was treated at 4° C. under argon with a solution of lithium diphenylphosphide [prepared from chlorodiphenylphosphine (13.36 g) and lithium metal (1.70 g) in dry THF (70 ml)]. The mixture was stirred for 5 minutes at 4° C., then for 3 hours at 50° C., cooled to 10° C. and poured into an ice-water mixture (300 ml). The aqueous mixture was washed with ether (2×100 ml), acidified to pH 3 with 2M hydrochloric acid and extracted with ether (3×100 ml). These combined extracts were washed successively with water (3×50 ml) and saturated brine (2×50 ml), then dried ($MgSO_4$) and evaporated). The oil obtained was purified by MPLC, eluting with hexane/ethyl acetate/acetic acid (75:25:1 v/v), to give 4(Z)-6-([2,4,5-cis]-4o-hydroxyphenyl-2-trifluoromethyl-1,3-dioxan-5-yl)hexenoic acid as a colourless oil (5.50 g); NMR (200 MHz): 1.87 (2H, m), 2.31 (4H, m), 2.60 (1H, m), 4.02 (1H, dm J=11 Hz), 4.25 (1H, br d J=11 Hz), 5.11 (1H, q J=3 Hz), 5.30 (1H, m), 5.33 (1H, d J=2 Hz), 5.44 (1H, m), 6.80 (1H, brd J=8 Hz), 6.93 (1H, td J=7, 1.5 Hz), 7.18 (2H, m) ppm; m/e 360 (M+).

The necessary starting material was obtained as follows:

(i) A solution containing (4.5-cis)-5-allyl-4-o-methoxyphenyl-2,2-dimethyl-1,3-dioxane (51.60 g), water (120 ml) and 2M hydrochloric acid (5.0 ml) in (THF) (400 ml) was heated with stirring at 70° C. for 2 hours. The mixture was poured into water (1 liter), then extracted with ether (3×500 ml). The combined extracts were washed with water (2×250 ml), then with brine (2×250 ml), dried (MgSO$_4$) and evaporated to give erythro-2-allyl-1-o-methoxyphenyl-1,3-propanediol (B) as a crystalline solid (43.69 g), m.p. 59°–60° C.

(ii) A solution of p-toluenesulphonyl chloride (43.4 g) in dichloromethane (120 ml) was added during 30 minutes to a stirred solution of B (44.69 g) in dichloromethane (400 ml) containing triethylamine (31.50 ml) and maintained at 4° C. The mixture was stirred for a further 1 hour at 4° C. and then for 64 hours at ambient temperature before being diluted with ether (1.2 l). The subsequent mixture was washed successively with water (2×200 ml), 0.2M aqueous hydrochloric acid (200 ml), saturated brine (200 ml), 2% w/v aqueous sodium hydrogen carbonate (200 ml), water (2×200 ml) and then with saturated brine (200 ml). The organic phase was dried (MgSO$_4$) and evaporated. The oil obtained was triturated with 5% v/v ethyl acetate/hexane to give a solid which was recrystallised from 1:3 v/v ethyl acetate/hexane (500 ml). There was thus obtained 3-(erythro-2-allyl-1-o-methoxyphenyl-1,3-propanediol) p-toluenesulphonate ester (C) (54.4 g), m.p. 103°–104° C.

(iii) A solution of C (54.4 g) in dry THF (600 ml) was treated with anhydrous trifluoroacetaldehyde (prepared from 50 g of trifluoroacetaldehyde methyl hemiacetal) at −78° C. under argon. The mixture was stirred for 1 hour at −78° C. allowed to warm to ambient temperature and stirred for a further 1 hour. Anhydrous potassium carbonate (38.72 g) was added and the stirred mixture was heated at 70° C. for 16 hours. The mixture was separated by filtration and the residue was washed with futher THF. Evaporation of the filtrate and flash chromatography of the residue, eluting with 2% v/v ethyl acetate/hexane, gave [2,4,5-cis]-5-allyl-4-o-methoxyphenyl-2-trifluoromethyl-1,3-dioxane (D) (35.0 g) as a crystalline solid, m.p. 43°–45° C.

(iv) Ozone was passed through a solution of D (35.0 g) in ethyl acetate (800 ml) at −78° C. until a permanent blue colour developed. The solution was then flushed with argon until colourless. A solution of triphenylphosphine (45.55 g) in ethyl acetate (200 ml) was added and the mixture was allowed to warm to ambient temperature overnight. After evaporation, ether (500 ml) was added to the residue and the insoluble triphenylphosphine oxide was removed by filtration. The filtrate was evaporated. The oil obtained was purified by flash chromatography, eluting with first 10% and then 25% v/v ethyl acetate/hexane, to give ([2,4,5-cis]-4-o-methoxyphenyl-2-trifluoromethyl-1,3-dioxan-5-yl)acetaldehyde (E) (33.25 g), m.p. 67°–68° C.

(v) A solution of E (9.88 g) in dry THF (60 ml) was added under argon to an ice-cooled, stirred solution of the ylid prepared from (3-carboxypropyl)triphenylphosphonium bromide (27.88 g) and potassium t-butoxide (14.56 g) in dry THF (300 ml). The mixture was stirred for 30 minutes at 4° C., then for 1 hour at ambient temperature and was then poured into ice-water (1 liter). The mixture obtained was washed with 50% v/v ether/hexane (2×250 ml) to remove the bulk of neutral material. The aqueous phase was acidified to pH 3 with 2M hydrochloric acid and extracted with ether (4×300 ml). The extracts were washed successively with water (3×150 ml) and saturated brine (2×100 ml), dried (MgSO$_4$) and evaporated. The yellow oil obtained was first purified by flash chromatography, eluting with toluene/ethyl acetate/acetic acid (87.5:12.5 v/v and then by MPLC, eluting with hexane/ethyl acetate/acetic acid (82:18:1 v/v). The clear oil thus obtained was triturated with hexane to give 4(Z)-6-([2,4,5-cis]-4-o-methoxyphenyl-2-trifluoromethyl-1,3-dioxan-5-yl)hexenoic acid as a crystalline solid (A) (7.30 g), m.p. 85°–86° C.; NMR (200 MHz); 1.63 (1H, m), 1.95 (1H, m), 2.30 (4H, m), 2.51 (1H, m), 3.82 (3H, s), 4.02 (1H, brd J=11 Hz), 4.20 (1H, br d J=11 Hz), 5.11 (1H, q J=3 Hz), 5.30 (1H, d J=2 Hz), 5.32 (2H, m), 6.85 (1H, d J=8 Hz), 7.00 (1H, t J=7 Hz), 7.27 (1H, td J=7, 2 Hz), 7.44 (1H, dd J=1.5 Hz); m/e 374 (M+).

EXAMPLE 2

The Wittig reaction described in part (v) of Example 1 may be carried out using ([2,4,5-cis]-4o-hydroxyphenyl-2-trifluoromethyl-1,3-dioxan-5-yl)acetaldehyde in place of the 4-o-methoxyphenyl analogue (E) to produce 4(Z)-6-([2,4,5-cis]-4-o-hydroxyphenyl-2-trifluoromethyl-1,3-dioxan-5-yl)hexanoic acid.

The requisite starting aldehyde may be obtained as follows:

(i) A solution of ([2,4,5-cis]-4-o-methoxyphenyl-2-trifluoromethyl-1,3-dioxan-5-yl)acetaldehyde (33.25 g) in dry THF (150 ml) was added under argon with stirring and ice-cooling to a solution of the ylid preparred from (4-carboxybutyl)triphenylphosphonium bromide (121.05 g) and potassium t-butoxide (61.21 g) in dry THF (750 ml). The mixture was stirred for 1 hour at 4° C., then overnight at ambient temperature and was then poured into ice-water (1.5 l). The mixture obtained was extracted with 50% v/v ether/hexane (2×500 ml) to remove the bulk of neutral material. The aqueous phase was then acidified to pH 2–3 with 2M hydrochloric acid and extracted with ether (4×400 ml). These combined extracts were washed with water(3×250 ml), then with saturated brine (2×200 ml), dried (MgSO$_4$) and evaporated to give a yellow oil. Purification by flash chromatography, eluting with toluene/ethyl acetate/acetic acid (85:15:2 v/v) gave a solid (40.15 g). Recrystallisation from hexane (600 ml) gave 5(Z)-7-([2,4,5-cis]-4-o-methoxyphenyl-2-trifluoromethyl-1,3-dioxan-5-yl)heptenoic acid (F) (36.2 g), m.p. 104°–105.5° C.

(ii) F (19.4 g) was added to a stirred solution of sodium thioethoxide (25.2 g) in dry 1,3-dimethyl-3,4,5,6-tetrahydro-2(1H)-pyrimidinone (DMPU) (300 ml) at 80°–85° C. under argon. The mixture was stirred for 2.25 hours, cooled to 10° C. and poured into an ice-water mixture (1 liter). The aqueous mixture was extracted with dichloromethane (2×500 ml), acidified to pH3 with 2M hydrochloric acid and extracted with ether (3×500 ml). The combined extracts were washed with water (3×300 ml), then with saturated brine (2×300 ml), then dried (MgSO$_4$) and the solvent evaporated. The oil obtained was purified by flash chromatography eluting with toluene/ethyl acetate/acetic acid (80:20:2 v/v). Recrystallisation from 15% v/v ether/hexane (150 ml) gave 5(Z)-7-([2,4,5-cis]-4-o-hydroxyphenyl-2-trifluoromethyl-1,3-dioxan-5-yl)heptenoic acid (G) (11.6 g), m.p. 93°–95° C.

(iii) Ozone was passed through a solution of (G) (1.22 g) in ethyl acetate (50 ml) at −78° C. until a permanent blue colour developed. The solution was then flushed with argon until colourless. A solution of triphenylphosphine (1.26 g) in ethyl acetate (20 ml) was then added and the mixture was stirred for 1 hour at −78° C. and then at ambient temperature overnight. The mixture was evaporated. The residue was purified by flash chromatography, eluting with 25% v/v ethyl acetate in hexane, to give ([2,4,5-cis]-4-o-hydroxyphenyl-2-trifluoromethyl-1,3-dioxan-5-yl)acetaldehyde (448 mg), m.p. 138°–140° C.; NMR: (200 MHz) 2.50 (1H, dd J=18, 3 Hz), 2.64 (1H, m), 2.98 (1H, dd J=18, 9 Hz), 4.20 (2H, m), 5.11 (1H, q J=3 Hz), 5.30 (1H, d J=2 Hz), 6.18 (1H, s), 6.80 (1H, dd J=8, 1 Hz), 6.93 (1H, td J=8, 1 Hz), 7.18 (2H, m), 9.60 (1H, s); m/e 290 (M+).

The starting aldehyde may also be obtained as follows:

(i) A solution of [2,4,5-cis]-5-allyl-4-o-methoxyphenyl-2-trifluoromethyl-1,3-dioxane (D) (1.22 g) in dry THF (4 ml) was treated at 4° C. under argon with a solution of lithium diphenylphosphide [prepared from chlorodiphenylphosphine (2.23 g) and lithium metal (283 mg) in dry THF (12 ml)]. The mixture was stirred for 15 minutes at 4° C., for 3 hours at 50° C., then cooled to 10° C. and poured into an ice-water mixture (50 ml). The aqueous mixture was acidified to pH 3 with 2M hydrochloric acid and extracted with ether (3×30 ml). The combined extracts were washed successively with water (4×15 ml) and saturated brine (15 ml), then dried (MgSO$_4$) and evaporated. The residual oil was purified by MPLC, eluting with hexane/ethyl acetate/acetic acid (82.5:17.5:0.1 v/v), to give [2,4,5-cis]-5-allyl-4-o-hydroxyphenyl-2-trifluoromethyl-1,3-dioxane (H), as a colourless oil which slowly crystallised to give solid (1.11 g), m.p. 80°–81.5° C.; NMR (200 MHz): 1.88 (1H, m), 2.00 (1H, m), 2.49 (1H, m), 4.02 (1H, dt J=12, 1.5 Hz), 4.33 (1H, dd J=12, 1 Hz), 5.05 (2H, m), 5.10 (1H, q J=3 Hz), 5.33 (1H, d J=2 Hz), 5.58 (1H, m), 6.41 (1H, s) 6.82 (1H, dd J=7, 1 Hz), 6.92 (1H, td J=7, 1 Hz), 7.11 (1H, dd J=7, 1.5 Hz), 7.20 (1H, td J=7, 1.5 Hz); m/e 306 (M+NH$_4$)+; calculated for $C_{14}H_{15}F_3O_3$: C, 58.3; H, 5.2%; found C, 58.1; H, 5.2%.

(ii) Ozone was passed through a solution of H (1.0 g) in ethyl acetate (75 ml) at −78° C. until a permanent blue colour developed. The solution was then flushed with argon until colourless. A solution of triphenylphosphine (1.37 g) in ethyl acetate (20 ml) was added and the mixture was stirred for 1 hour at −78° C. and then overnight at ambient temperature. The solvent was evaporated and the residue was purified by flash chromatography, eluting with 30% v/v ethyl acetate/hexane, to give ([2,4,5-cis]-4-o-hydroxyphenyl-2-trifluoromethyl-1,3-dioxan-5-yl)acetaldehyde as a crystalline solid (766 mg), m.p. 140°–142° C.; NMR (200 MHz): 2.51 (1H, br dd J=18, 3 Hz), 2.64 (1H, m), 2.98 (1H, dd J=18, 9 Hz), 4.19 (2H, m), 5.11 (1H, q J=3 Hz), 5.32 (1H, d J=2 Hz), 6.17 (1H, s), 6.79 (1H, br d J=8 Hz), 6.93 (1H, td J=7, 1 Hz), 7.19 (2H, m), 9.61 (1H, s).

EXAMPLE 3

The following illustrate representative pharmaceutical dosage forms containing the compound of formula I in racemic or laevorotatory optically active form, or a salt thereof (hereafter compound X) for therapeutic or prophylactic use in humans:

| (a) Tablet I | mg/tablet |
|---|---|
| Compound X | 100 |
| Lactose Ph. Eur. | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound X | 50 |
| Lactose Ph. Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
|---|---|
| Compound X | 1.0 |
| Lactose Ph. Eur | 93.25 |
| Croscarmellose sodium | 4.0 |
| Maize starch paste (5% w/v paste) | 0.75 |
| Magnesium stearate | 1.0 |

| (d) Capsule | mg/capsule |
|---|---|
| Compound X | 10 mg |
| Lactose Ph. Eur. | 488.5 |
| Magnesium stearate | 1.5 |

| (e) Injection I | (50 mg/ml) |
|---|---|
| Compound X (free acid form) | 5.0% w/v |
| 1M Sodium hydroxide solution | 15.0% v/v |
| 0.1M Hydrochloric acid (to adjust pH to 7.6) | |
| Polyethylene glycol 400 | 4.5% w/v |
| Water for injection to 100% | |

| (f) Injection II | (10 mg/ml) |
|---|---|
| Compound X (free acid form) | 1.0% w/v |
| Sodium phosphate EP | 3.6% w/v |
| 0.1M Sodium hydroxide solution | 15.0% v/v |
| Water for injection to 100% | |

| (g) Injection III | (1 mg/ml, buffered to pH 6) |
|---|---|
| Compound X (free acid form) | 0.1% w/v |
| Sodium phosphate BP | 2.26% w/v |
| Citric acid | 0.38% w/v |
| Polyethylene glycol 400 | 3.5% w/v |
| Water for injection to 100% | |

| (h) Aerosol I | mg/ml |
|---|---|
| Compound X | 10.0 |
| Sorbitan trioleate | 13.5 |
| Trichlorofluoromethane | 910.0 |
| Dichlorodifluoromethane | 490.0 |

| (i) Aerosol II | mg/ml |
|---|---|
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

| (j) Aerosol III | mg/ml |
|---|---|
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |

| (k) Aerosol IV | mg/ml |
|---|---|
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

Note

The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

Scheme 1

[$R^1 \neq$ acyl]

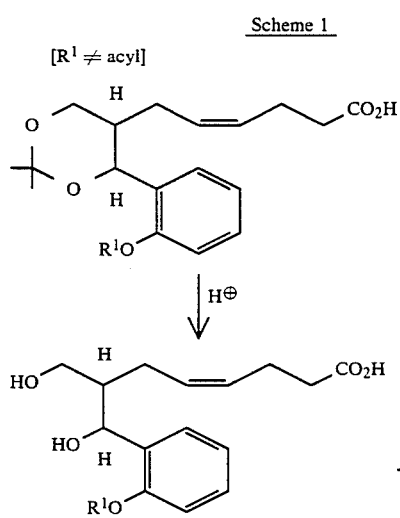

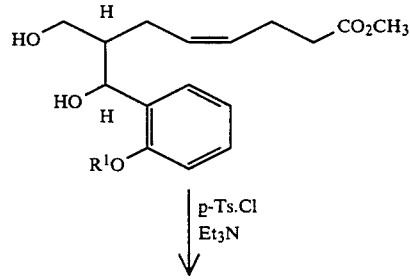

-continued
Scheme 1

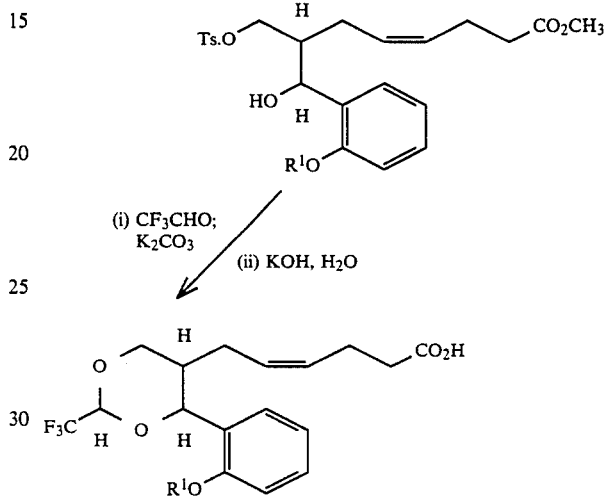

|  | Chemical Formulae |
|---|---|
| 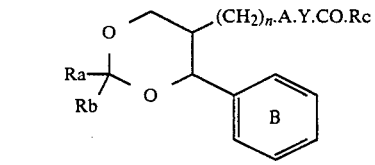 | Z |
| 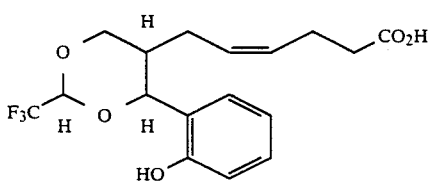 | I |
| 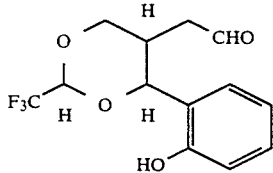 | II |
| 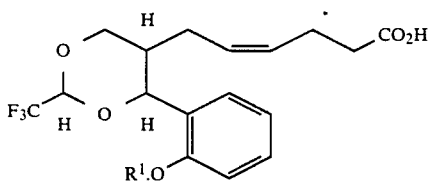 | III |

| | Chemical Formulae |
|---|---|
| 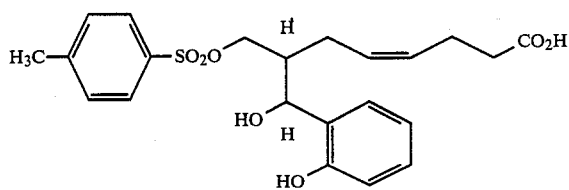 | IV |
| 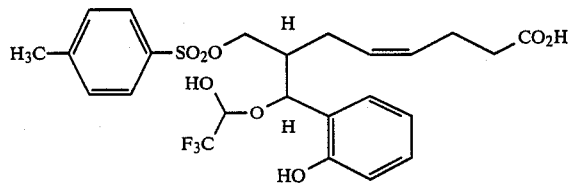 | V |

What is claimed is:

1. The compound 4(Z)-6-((2,4,5-cis)-4-o-hydroxyphenyl-2-trifluoromethyl-1,3-dioxan-5-yl)hexenoic acid of the formula I:

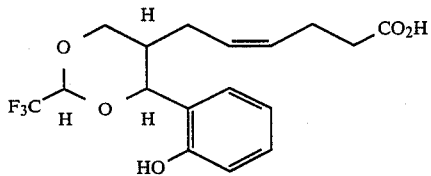   I or a pharmaceutically acceptable salt thereof.

2. The racemic form of the compound claimed in claim 1; or a pharmaceutically acceptable salt thereof.

3. A salt as claimed in claim 1 or 2 which is selected from alkali metal, alkaline earth metal, aluminium and ammonium salts, and from salts with organic amines and quaternary bases forming physiologically acceptable cations.

4. A salt as claimed in claim 3 which is selected from sodium, potassium, magnesium, calcium, aluminium and ammonium salts, and from salts with methylamine, dimethylamine, trimethylamine, ethylenediamine, piperidine, morpholine, pyrrolidine, piperazine, ethanolamine, triethanolamine, N-methylglucamine, tetramethylammonium hydroxide and benzyltrimethylammonium hydroxide.

5. A method of antagonising one or more of the actions of thromboxane $A_2$ in a warm-blooded animal requiring such treatment which comprises administering to said animal an effective amount of the compound of formula I, or a pharmaceutically acceptable salt thereof, as defined in claim 1.

6. A pharmaceutical composition suitable for antagonising one or more actions of thromboxane $A_2$ comprising an effective amount of the compound of formula I or a pharmaceutically acceptable salt thereof as claimed in claim 1, together with a pharmaceutically acceptable diluent or carrier.

* * * * *